United States Patent
Wall, Jr.

(10) Patent No.: US 10,974,026 B1
(45) Date of Patent: *Apr. 13, 2021

(54) TISSUE TRANSFER DEVICES SUITABLE FOR TISSUE IMPLEMENTATION

(71) Applicant: Simeon Wall, Jr., Shreveport, LA (US)

(72) Inventor: Simeon Wall, Jr., Shreveport, LA (US)

(73) Assignee: Surgistem Technologies LLC, Boston, MA (US)

( * ) Notice: Subject to any disclaimer, the term of this patent is extended or adjusted under 35 U.S.C. 154(b) by 76 days.

This patent is subject to a terminal disclaimer.

(21) Appl. No.: 15/230,997

(22) Filed: Aug. 8, 2016

Related U.S. Application Data

(62) Division of application No. 14/173,021, filed on Feb. 5, 2014, now Pat. No. 9,433,727.

(51) Int. Cl.
  *A61M 5/142* (2006.01)
  *A61M 25/00* (2006.01)
  *A61B 17/22* (2006.01)
  *A61B 17/00* (2006.01)

(52) U.S. Cl.
  CPC ......... *A61M 25/0074* (2013.01); *A61B 17/22* (2013.01); *A61M 5/14212* (2013.01); *A61B 2017/00424* (2013.01); *A61B 2017/00969* (2013.01)

(58) Field of Classification Search
  CPC ................................................ A61M 25/0074
  See application file for complete search history.

(56) References Cited

U.S. PATENT DOCUMENTS

| | | | |
|---|---|---|---|
| 5,882,340 A * | 3/1999 | Yoon | A61B 17/3417 604/104 |
| 6,196,839 B1 | 3/2001 | Ross | |
| 6,733,442 B1 | 5/2004 | Larnard | |
| 2005/0187555 A1 | 8/2005 | Biedermann et al. | |
| 2005/0261670 A1 | 11/2005 | Weber et al. | |
| 2006/0083720 A1 * | 4/2006 | Fraser | C12N 5/0653 424/93.7 |
| 2006/0293647 A1 * | 12/2006 | McRae | A61B 18/1492 606/27 |
| 2008/0051891 A1 * | 2/2008 | Malandain | A61B 17/025 623/17.11 |
| 2008/0167613 A1 * | 7/2008 | Khouri | A61M 1/0009 604/119 |
| 2009/0131925 A1 | 5/2009 | Tempel et al. | |
| 2010/0100114 A1 | 4/2010 | Berger | |
| 2011/0144428 A1 | 6/2011 | Morningstar et al. | |
| 2012/0203220 A1 | 8/2012 | Brannan et al. | |
| 2013/0310749 A1 | 11/2013 | Del Vecchio | |

* cited by examiner

*Primary Examiner* — Bin Shen
(74) *Attorney, Agent, or Firm* — R. Keith Harrison

(57) ABSTRACT

Tissue transfer devices suitable for transfer of tissues include a cannula, a plurality of tissue separating members outwardly extendable from the cannula, a tissue reservoir disposed in fluid communication with the cannula and a pump disposed in fluid communication with the tissue reservoir.

9 Claims, 10 Drawing Sheets

US 10,974,026 B1

TISSUE TRANSFER DEVICES SUITABLE FOR TISSUE IMPLEMENTATION

CROSS-REFERENCE TO RELATED APPLICATIONS

This is a divisional application of U.S. non-provisional application Ser. No. 14/173,021, filed Feb. 5, 2014 and entitled TISSUE REJUVENATION METHODS AND TISSUE TRANSFER DEVICES SUITABLE FOR IMPLEMENTATION THEREOF, which claims the benefit of U.S. provisional application No. 61/760,846, filed Feb. 5, 2013 and entitled TISSUE REJUVENATION METHODS AND TISSUE TRANSFER DEVICES SUITABLE FOR IMPLEMENTATION THEREOF, each of which provisional application and non-provisional application is hereby incorporated by reference herein in its entirety.

FIELD

Illustrative embodiments of the disclosure generally relate to tissue transfer devices suitable for transferring body tissues. More particularly, illustrative embodiments of the disclosure relate to tissue transfer devices suitable for implementation of tissue rejuvenation methods in which body tissues can be repaired, regenerated or renewed by removing tissue regenerative cells from a cell harvest site, mechanically agitating the cells and injecting the cells at a cell injection site in an area on a patient which is in need of rejuvenation due to injury, disease, wear, aging and/or other causes.

BACKGROUND

The background description provided herein is solely for the purpose of generally presenting the context of the illustrative embodiments of the disclosure. Aspects of the background description are neither expressly nor impliedly admitted as prior art against the claimed subject matter.

Skin, adipose and other body tissues may change in appearance and/or lose function with age and/or use due to injury, disease, wear, aging and/or other causes. One of the goals of plastic surgical procedures may include rejuvenation of body tissues to restore the original appearance and/or function of the tissues. For example, conventional tissue rejuvenation procedures may include the use of adipose stem/progenitor cells to promote angiogenesis and adipose tissue regeneration. However, such procedures may have less-than-optimum results and scarring.

Accordingly, tissue transfer devices suitable for implementation of tissue rejuvenation methods in which body tissues can be repaired, regenerated or renewed by removing tissue regenerative cells from a cell harvest site, mechanically agitating the cells and injecting the cells at a cell injection site in an area on a patient which is in need of rejuvenation due to injury, disease, wear, aging and/or other causes are needed.

SUMMARY

Illustrative embodiments of the disclosure are generally directed to tissue rejuvenation devices. An illustrative embodiment of the tissue rejuvenation devices includes a cannula, a plurality of tissue separating members outwardly extendable from the cannula, a tissue reservoir disposed in fluid communication with the cannula and a pump disposed in fluid communication with the tissue reservoir.

BRIEF DESCRIPTION OF THE DRAWINGS

Illustrative embodiments of the disclosure will now be described, by way of example, with reference to the accompanying drawings, in which.

DETAILED DESCRIPTION

Figure 1:
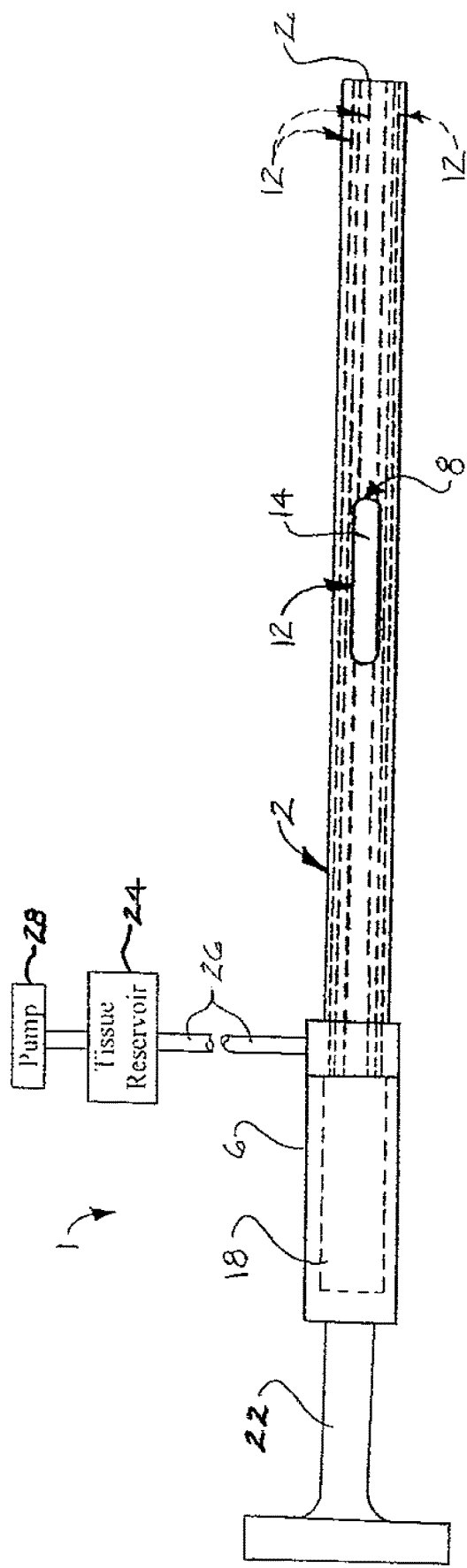
FIG. 1 is a partially schematic side view of an illustrative embodiment of the tissue transfer devices.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the claims.

Moreover, the illustrative embodiments described herein are not exhaustive and embodiments or implementations other than those which are described herein and which fall within the scope of the appended claims are possible. Furthermore, them is no intention to be bound by any expressed or implied theory presented in the preceding technical field, background, brief summary or the following detailed description.

In the regeneration of adipose tissue, adipose-resident perivascular progenitor cells (adipose-derived stromal cells, or ASCs) work together with vascular endothelial cells (VECs) and stem/progenitor cells recruited from bone marrow. ASCs are capable of differentiating into adipocytes or VECs and releasing angiogenic growth factors. In adipose tissue, adipocytes are attached to capillaries. The high $pO_2$ of adipose tissue reflects the high density of capillary networks of the tissue. When adipose tissue is subjected to severe ischemia, adipocytes die first, followed by VECs and blood-derived cells. By contrast, ASCs can survive severe ischemia for up to 3 days, during which time they are activated and contribute to the adaptive repair process through adipogenesis and angiogenesis. Under circumstances in which ASCs and stem cells die, the adipose tissue loses the ability to regenerate and becomes necrotic, leading to macrophage activation and infiltration, tissue atrophy and scar formation.

Pericytes are perivascular cells which wrap around the exterior of blood capillaries and play an active role in angiogenesis. In a process known as "compensatory proliferation", apoptotic or injured cells release signals which activate ASCs to replenish the apoptotic or injured cells with new cells. Upon activation of ASCs after injury, soluble factors may be released from apoptotic cells, injured cells and/or damaged extracellular matrix to recruit stem/progenitor cells from bone marrow and mediate the compensatory proliferation and differentiation of ASCs into adipocytes, leading to subsequent repair of the adipose tissue. These factors are released at different phases or stages of tissue repair and may include basic FGF (bFGF), PDGF, EGF TGF-β, VEGF, HGF, IL-8, matrix metalloproteinase-1, KGF, IL-6 and matrix metalloproteinase-8, for example and without limitation. Injured pericytes release soluble factors which promote angiogenesis of the affected tissue.

The differentiation pathways of ASCs are determined by external signals such as death of adjacent cells, ECM disruption, bleeding, inflammation, hypoxia, cytokines, chemokine, tissue injury and mechanical force. Quiescent ASCs can be activated via tissue wounding. Therefore, by the damage or removal of tissue, resident ASCs and pericytes can be activated to reconstruct or renew the entire tissue in collaboration with infiltrated stem cells from the bone marrow.

Illustrative embodiments of the disclosure are generally directed to tissue transfer devices and methods for repairing, regenerating or renewing body tissues which are in need of rejuvenation due to injury, disease, wear, aging and/or other causes. Illustrative embodiments of the methods may include removing tissue regenerative cells from a cell harvest site and mechanically agitating and injecting the cells at a cell injection site which is remote from the cell harvest site on a patient without inducing apoptosis in the cells. The injured and injected tissue regenerative cells may include ASCs and pericytes which release soluble factors that recruit resident tissue regenerative cells as well as infiltrate stem cells from bone marrow to repair, regenerate or renew the tissues in the area of the cell injection site. The methods may be used to facilitate non-thermal and non-destructive removal of pericytes from capillaries at the cell injection site and implantation of the harvested pericytes at the cell injection site, resulting in rejuvenation of body tissues at the cell injection site with little or no scarring.

While the methods are particularly effective in the repair, regeneration or renewal of adipose tissue, the methods may be equally adaptable to repair, regeneration or renewal of other types of body tissues including but not limited to muscle, bone and fascia. As used herein, "tissue regenerative cells" may include but are not limited to adipose-derived stem cells (ASCs), pericytes and stem cells from bone marrow which infiltrate the tissues at the cell injection site and mediate release of soluble factors that stimulate adipogenesis and angiogenesis in the body tissue which is subjected to rejuvenation treatment.

Referring initially to FIGS. 1-5 of the drawings, an illustrative embodiment of the tissue transfer devices, hereinafter device, is generally indicated by reference numeral 1. The device 1 may include a cannula 2. In some embodiments, the cannula 2 may have a cannula wall 3 which encloses a cannula interior 4. The cannula 2 may be generally elongated and cylindrical and may include a medical-grade plastic, metal and/or other material which is medically compatible and consistent with the functional requirements of the device 1. In some embodiments, the cannula 2 may have a diameter of about 2.5 mm or less.

Figure 4:
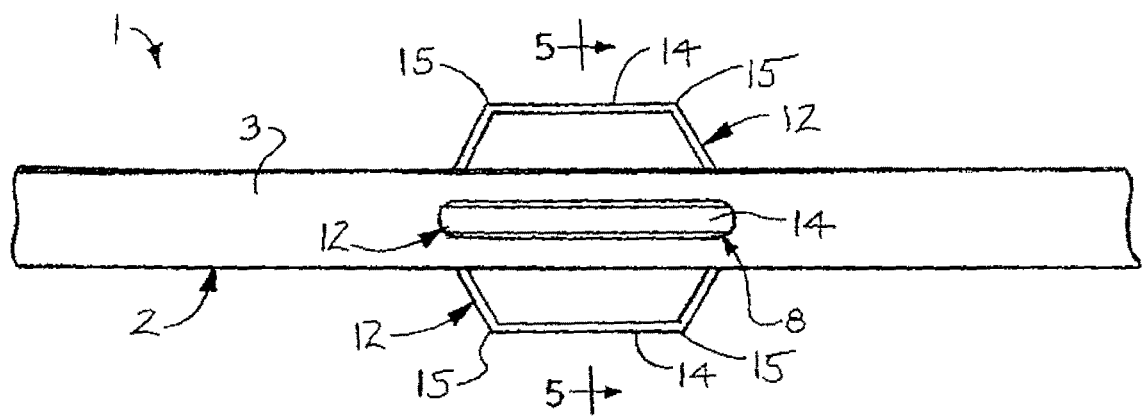
FIG. 4 is a side view, partially in section, of the sectioned portion of the illustrative device illustrated in FIG. 1, with the tissue separating members deployed in the expanded configuration.
Figure 5:
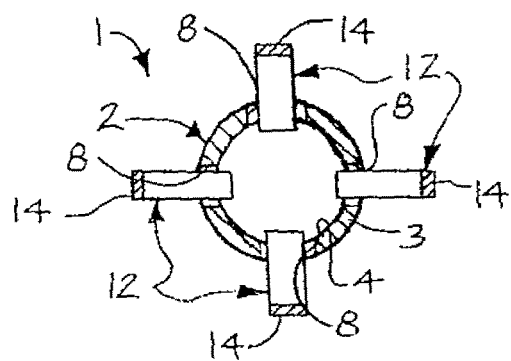
FIG. 5 is a cross-sectional view, taken along section lines 5-5 in FIG. 4.
Figure 6:
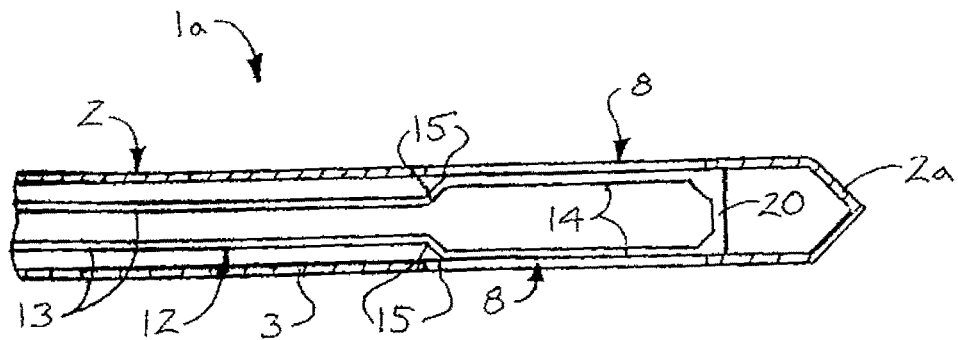
FIG. 6 is a longitudinal sectional view of a sectioned portion of an alternative illustrative embodiment of the tissue transfer devices, with the tissue separating members of the device deployed in a collapsed or retracted configuration.
Figure 7:
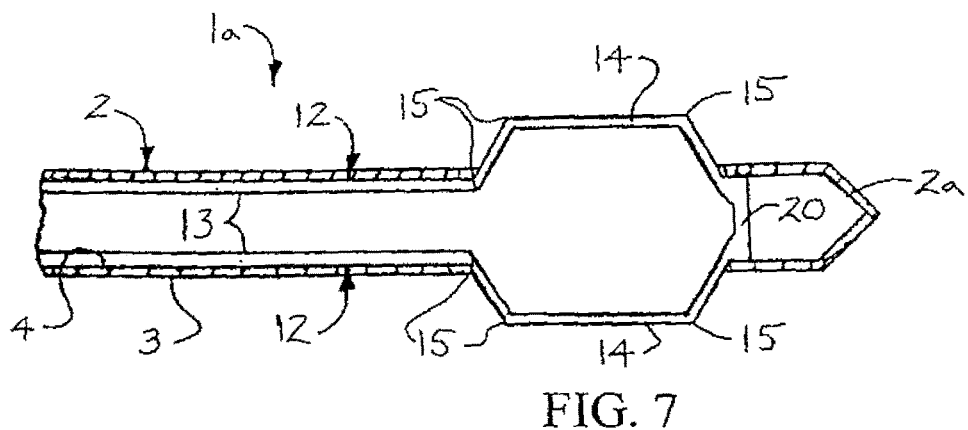
FIG. 7 is a longitudinal sectional view of the sectioned portion of the illustrative device illustrated in FIG. 6, with the tissue separating members deployed in an expanded, tissue-separating configuration.
Figure 8:
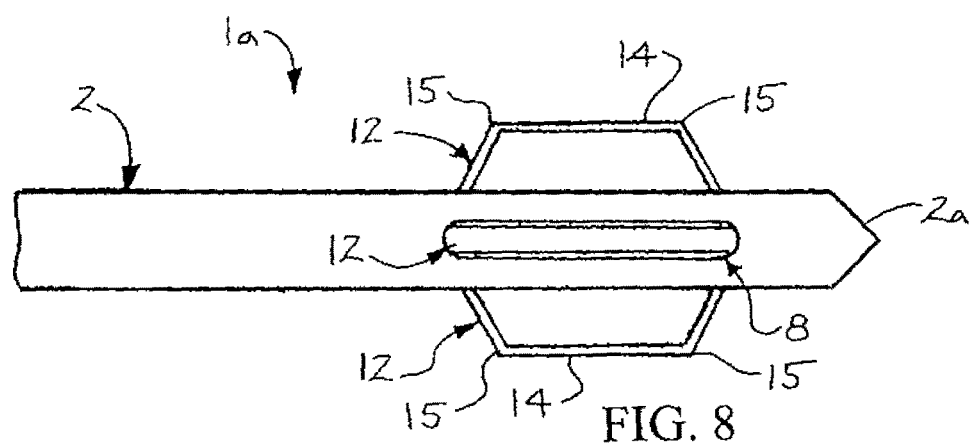
FIG. 8 is a side view of the sectioned portion of the illustrative device illustrated in FIG. 6, with the tissue separating members deployed in the expanded configuration.
Figure 9:
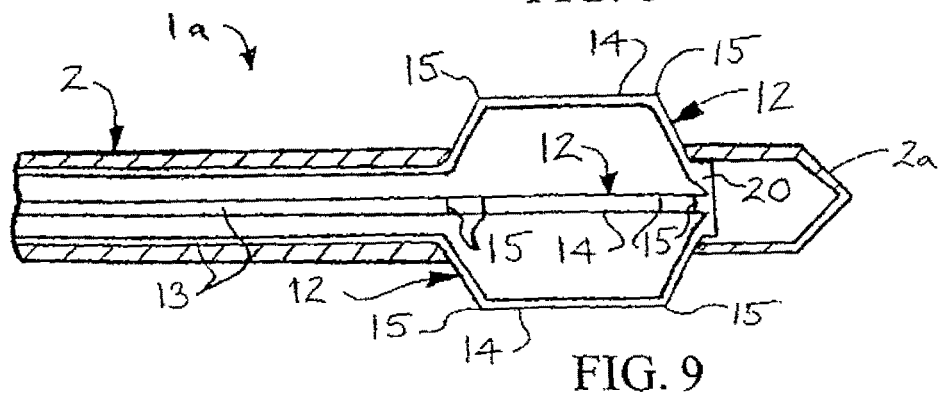
FIG. 9 is a longitudinal interior view of the sectioned portion of the illustrative device illustrated in FIG. 6, with the tissue separating members deployed in the expanded configuration.

Multiple expansion segment openings 8 may extend through the cannula wall 3 at selected locations along the length and the circumference of the cannula 2. As illustrated in FIGS. 1 and 4, each expansion segment opening 8 may have a generally elongated, slotted shape. As illustrated in FIG. 5, in some embodiments of the device 1, four expansion segment openings 8 may extend through the cannula wall 3 generally at 90 degrees with respect to each other around the cross-sectional circumference of the cannula wall 3.

Multiple tissue separating members 12 may extend longitudinally through the cannula interior 4 of the cannula 2. In some embodiments, four tissue separating members 12 may be arranged around the circumference of the cannula 2 at the positions of the respective expansion segment openings 8. Each tissue separating member 12 may include an elongated rod or strip of flexible metal or other material with an elongated proximal shaft segment 13, an elongated distal shaft segment 13a and at least one expansion segment 14 extending between the proximal shaft segment 13 and the distal shaft segment 13a. Bend lines 15 may be formed or shaped in the tissue separating member 12 to demarcate respective ends of each expansion segment 14 from the proximal shaft segment 13 and the distal shaft segment 13a. The expansion segment or segments 14 of each tissue separating member 12 may generally register with a corresponding tissue separating member opening or openings 8 in the cannula wall 3.

Figure 2:
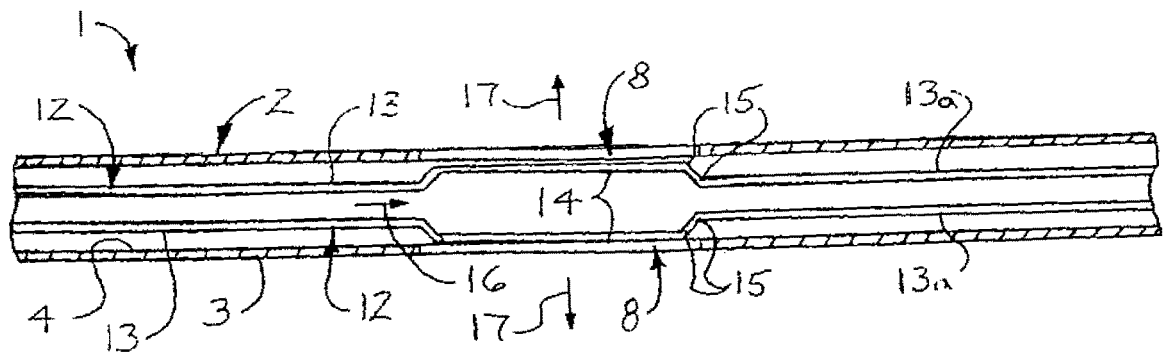
FIG. 2 is a longitudinal sectional view of a sectioned portion of the illustrative device illustrated in FIG. 1, with multiple tissue separating members of the device deployed in a collapsed or retracted configuration.
Figure 3:
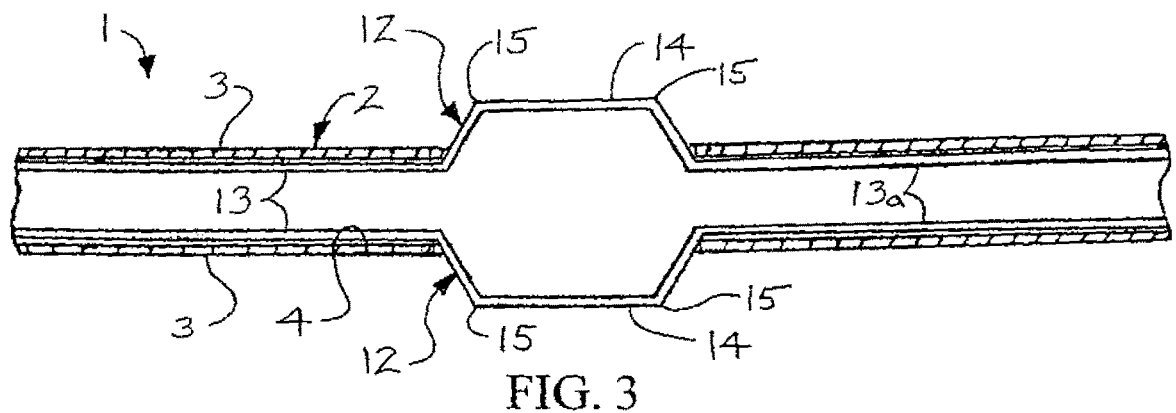
FIG. 3 is a longitudinal sectional view of the sectioned portion of the illustrative device illustrated in FIG. 1, with the tissue separating members deployed in an expanded, tissue-separating configuration.

The proximal shaft segment 13 is slidably disposed whereas the distal shaft segment 13a of each tissue separating member 12 is stationary in the cannula interior 4. Accordingly, upon sliding movement of the proximal shaft segment 13 of each tissue separating member 12 along the longitudinal axis of the cannula 2 in the cannula interior 4 in the direction indicated by the arrow 16 in FIG. 2, relative to the stationary distal shaft segment 13a, the expansion segment 14 bends along the bend lines 15 and expands or buckles outwardly through the expansion segment opening 8, as indicated by the arrows 17 in FIG. 2 and as illustrated in FIG. 3. Conversely, upon sliding movement of the tissue separating member 12 in the direction which is opposite the arrow 16, the expansion segment 14 is retracted back into the corresponding expansion segment opening 8 as illustrated in FIG. 2.

As illustrated in FIG. 1, the cannula 2 may extend from a cannula base 6. The cannula base 6 may be part of a hand piece (not illustrated) which can be grasped by an operator of the device 1 to facilitate selective deployment of the tissue separating members 12. A driving mechanism 18 may operably engage each tissue separating member 12 to facilitate selective bidirectional movement of the tissue separating member 12 in the cannula 2. The driving mechanism 18 may be any type of mechanism which is operable to engage and move the tissue separating members 12 along the longitudinal axis of the cannula 2 as indicated by the arrow 16 in FIG. 2. For example and without limitation, in some embodiments, the driving mechanism 18 may include a threaded screw mechanism which engages the tissue separating members 12. Accordingly, the screw mechanism can be selectively threaded toward and against the tissue separating members 12 to actuate displacement of the proximal shaft segments 13 in the cannula interior 4 and expand the expansion segments 14 through the respective expansion segment openings 8. The screw mechanism can be selectively unthreaded, allowing the proximal shaft segments 13 of the tissue separating members 12 to recoil or straighten and retract the expansion shaft segments 14 back into the respective expansion segment openings 8. In some embodiments, a locking device (not illustrated) may operably engage the tissue separating members 12 for the purpose of selectively locking the tissue separating members 12 in the expanded, functionally-deployed position according to the knowledge of those skilled in the art. A handle 22 may extend from the cannula base 6 to facilitate manual manipulation of the device 1.

As further illustrated in FIG. 1, a tissue reservoir 24 may be disposed in fluid communication with the cannula 2 such as through a tissue reservoir conduit 26. A pump 28 may be disposed in fluid communication with the tissue reservoir 24. The pump 28 is operable to selectively apply a partial vacuum or negative pressure 54 (FIG. 14) or positive pressure 55 (FIG. 18) to the cannula interior 4 and the expansion segment openings 8 (FIG. 2) in the cannula 2 for purposes which will be hereinafter described.

Figure 10:
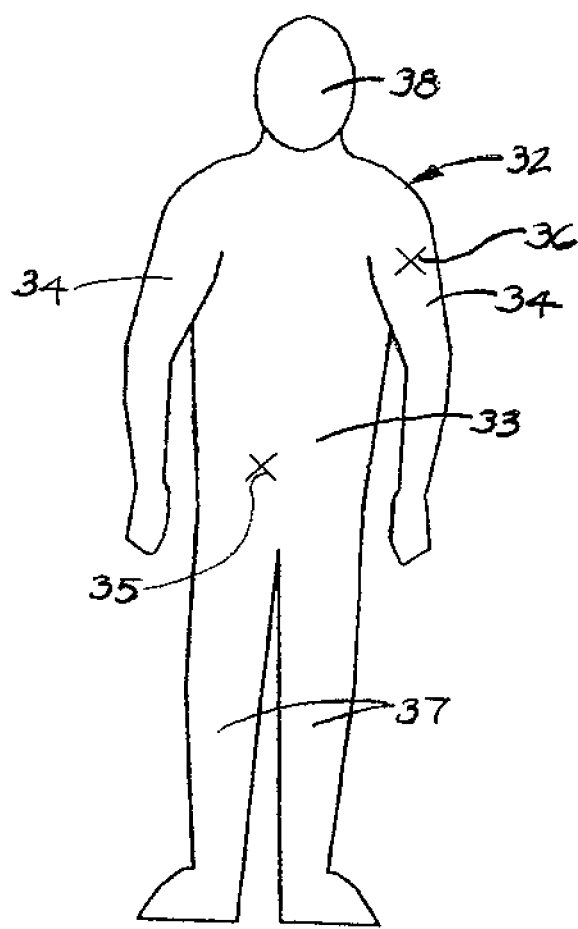
FIG. 10 is a front view of a patient, more particularly illustrating a cell harvest site and a cell injection site marked on the patient in implementation of an illustrative embodiment of the tissue rejuvenation methods.

Referring next to FIGS. 10-18 of the drawings, in exemplary application, the device 1 is used to harvest tissue regenerative cells 49 (FIG. 15A) from harvest site adipose tissue 35a (FIGS. 12-15) at a cell harvest site 35 (FIG. 10) on a patient 32 and inject the tissue regenerative cells 49 into injection site adipose tissue 36a (FIGS. 16-18) at a cell injection site 36 on the patient 32 to rejuvenate the injection site adipose tissue 36a at the cell injection site 36. Accordingly, as illustrated in FIG. 10, the cell harvest site 35 and the cell injection site 36 may initially be identified and marked on the patient 32. The cell harvest site 35 may be any site on the patient 32 which includes tissue regenerative cells 49 that can be harvested for injection into the cell injection site 36. The cell injection site 36 may be any site on the patient 32 which is in need of rejuvenation due to injury, disease, wear, aging and/or other causes. In the example illustrated in FIG. 10, the cell harvest site 35 is on the abdomen 33 and the cell injection site 36 is on the left arm 34 of the patient 32. However, it will be recognized and understood that the cell harvest site 35 and the cell injection site 36 may be any location on the patient 32 which is in need of rejuvenation whether on the abdomen 33, arm 34, leg 37, face 38 or other area, and the cell harvest site 35 may be any location on the patient 32 from which the tissue regenerative cells 49 can be harvested for injection into the cell injection site 36. The tissue regenerative cells 49 may include but are not limited to adipose-derived stem cells (ASCs), pericytes 52 (FIG. 15A) and stem cells from bone marrow which infiltrate the tissues at the cell injection site 36 and mediate release of soluble factors that stimulate adipogenesis and angiogenesis in the cell injection site adipose tissue 36a.

Figure 11:
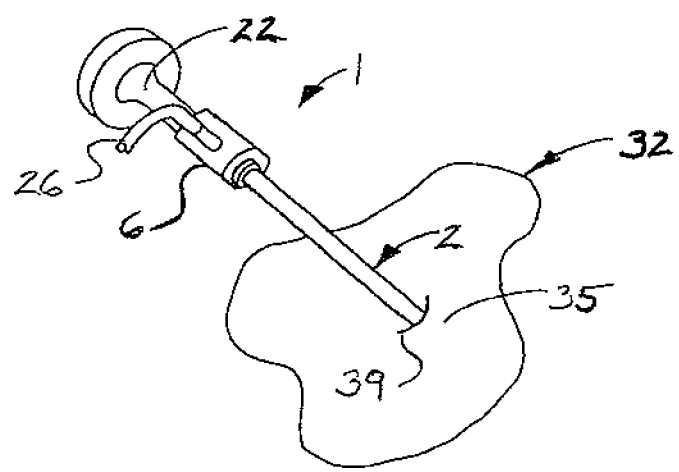
FIG. 11 is a perspective view of an illustrative embodiment of the tissue transfer devices, inserted in the patient at the cell harvest site in the harvesting of tissue regenerative cells from the cell harvest site in implementation of an illustrative embodiment of the tissue rejuvenation methods.
Figure 12:
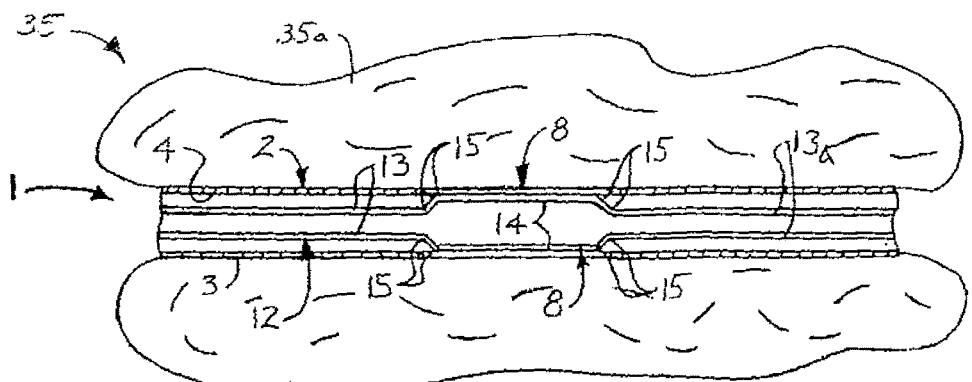
FIG. 12 is a longitudinal sectional view of the sectioned portion of the illustrative tissue transfer device illustrated in FIG. 1 inserted between adjacent portions of adipose tissue at the cell harvest site preparatory to separation of the adipose tissue portions, with the tissue separating members of the device initially deployed in the retracted configuration.
Figure 13:
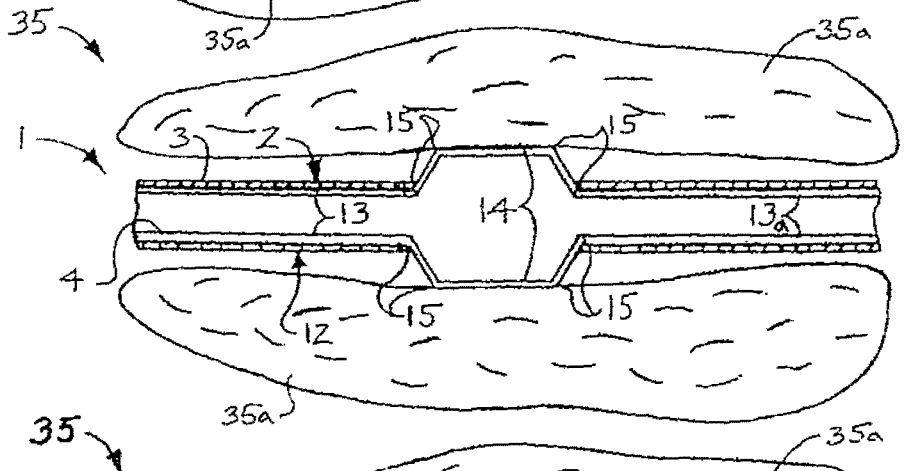
FIG. 13 is a longitudinal sectional view of the sectioned portion of the illustrative tissue transfer device illustrated in FIG. 1, with the tissue separating members of the device deployed in the expanded configuration and separating the adjacent portions of adipose tissue from each other.

As illustrated in FIG. 11, a small incision 39 is made in the skin of the patient 32 at the cell harvest site 35, and the cannula 2 is inserted through the incision 39. The driving mechanism 18 (FIG. 1) of the device 1 is operated to axially move each tissue separating member 12 in the cannula 2 in the direction indicated by the arrow 16 in FIG. 2. This linear actuation causes the expansion segments 14 to buckle or expand within the tissue separating members 12 through the respective expansion segment openings 8 to engage and separate the portions of harvest site adipose tissue 35a from each other, as illustrated in FIGS. 13 and 14.

Figure 14:
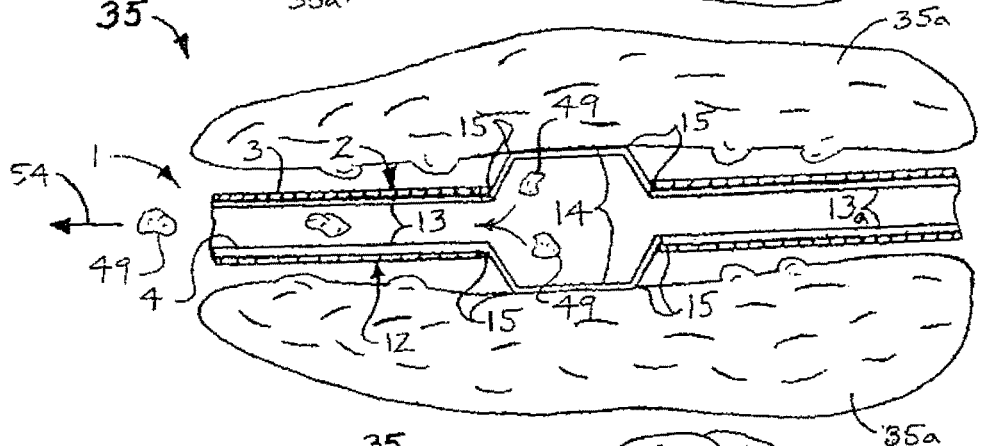
FIG. 14 is a longitudinal sectional view of the sectioned portion of the illustrative tissue transfer device illustrated in FIG. 1, with the tissue separating members of the device deployed in the expanded configuration and more particularly illustrating aspiration of tissue regenerative cells from the cell harvest site after separation of the tissue.
Figure 15:
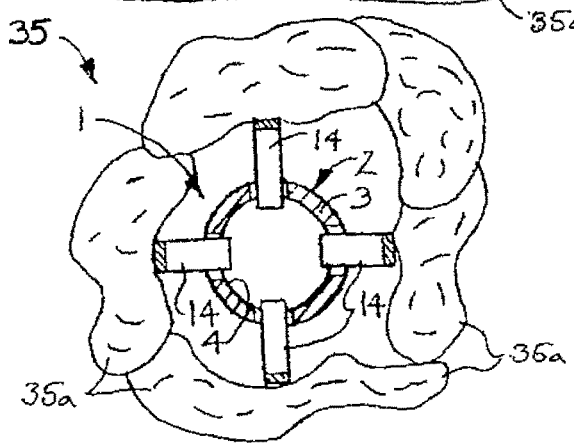
FIG. 15 is a cross-sectional view of the illustrative tissue transfer device illustrated in FIG. 14, with the tissue separating members of the device deployed in the expanded configuration and separating the adjacent portions of adipose tissue from each other.
Figure 15A:
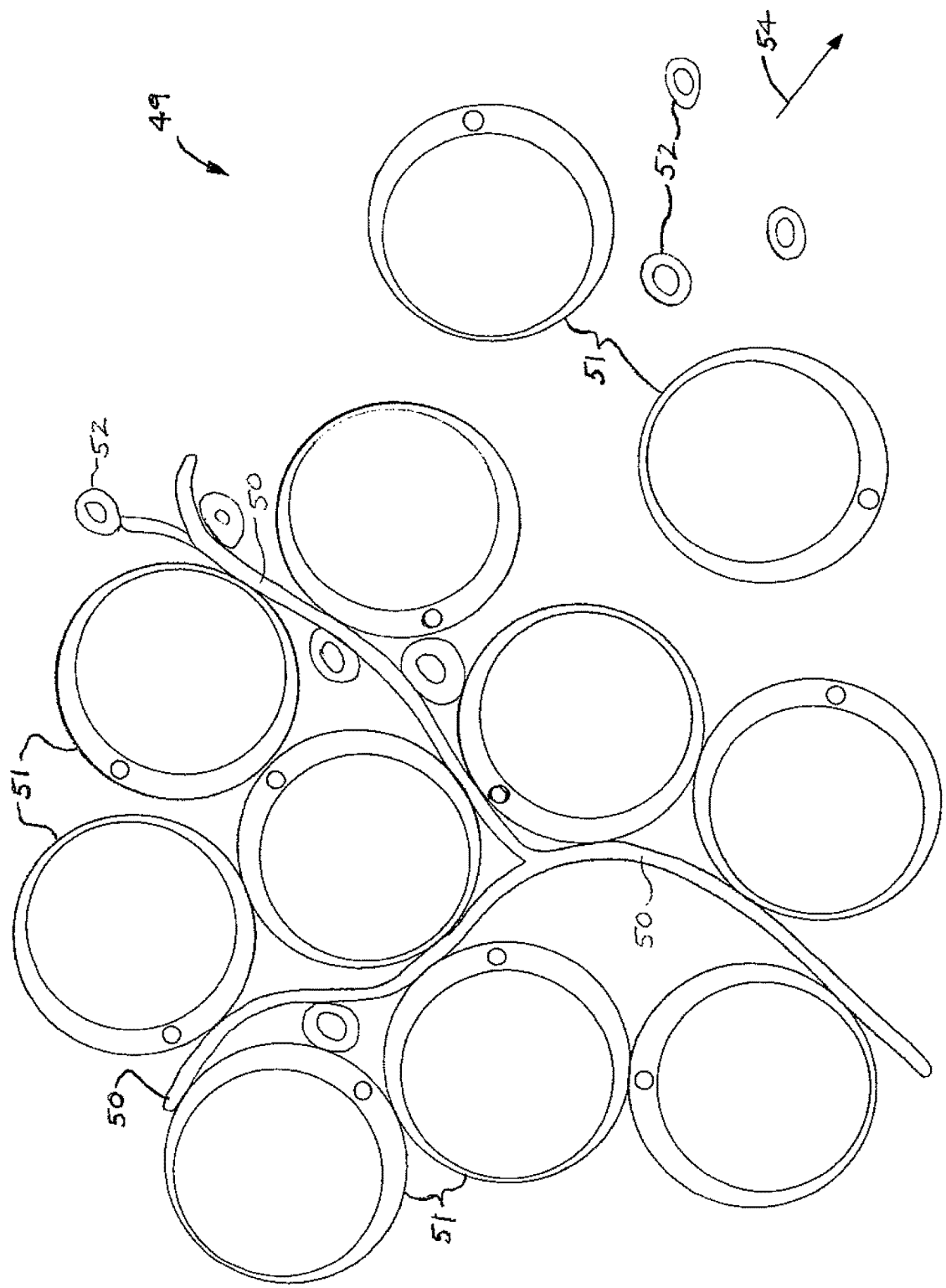
FIG. 15A is a diagram which illustrates removal of tissue regenerative cells from capillaries at a cell harvest site in implementation of an illustrative embodiment of the tissue rejuvenation methods.
Figure 16:
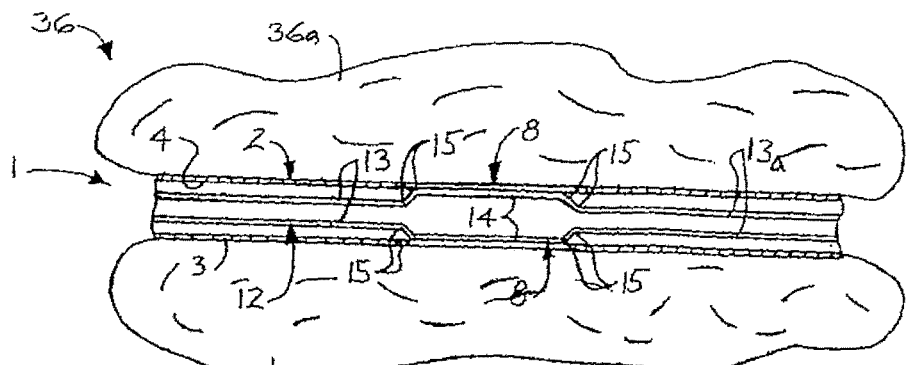
FIG. 16 is a longitudinal sectional view of the sectioned portion of the illustrative tissue transfer device illustrated in FIG. 1 inserted between adjacent portions of adipose tissue at the cell injection site, with the tissue separating members of the device initially deployed in the retracted configuration preparatory to separation of the adipose tissue portions.

As illustrated in FIG. 14, the pump 28 (FIG. 1) may be operated to draw negative pressure 54 on the cannula interior 4 and aspirate tissue regenerative cells 49 through the expansion segment openings 8 and/or other opening (not illustrated) in the cannula 2, the cannula interior 4, the tissue reservoir conduit 26 and into the tissue reservoir 24, respectively. As illustrated in FIG. 15A, the tissue regenerative cells 49 may include adipocytes 51 and pericytes 52 which receive blood supply from capillaries 50. The negative pressure 54 which is applied by the pump 28 (FIG. 1) of the device 1 pulls or aspirates the adipocytes 51 and pericytes 52 from the capillaries 50 through the cannula 2 and tissue reservoir conduit 26 and into the tissue reservoir 24, respectively. These actions and movements of the adipocytes 51 and pericytes 52 slightly injure without inducing apoptosis in the cells. After the desired quantity of tissue regenerative cells 49 has been harvested from the cell harvest site 35 and collected in the tissue reservoir 24, the driving mechanism 18 (FIG. 1) may be operated to release the tissue separating members 12 and return the expansion segments 14 to the retracted position, as illustrated in FIG. 16, and the cannula 2 withdrawn from the incision 39 (FIG. 11).

Figure 17:
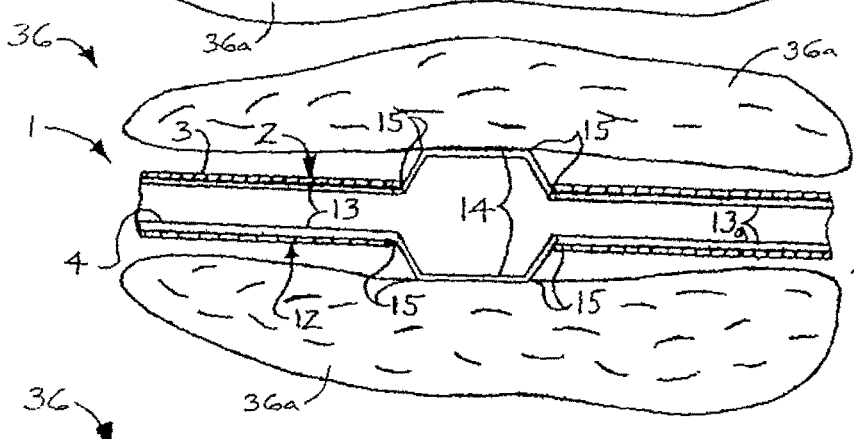
FIG. 17 is a longitudinal sectional view of the sectioned portion of the illustrative tissue transfer device illustrated in FIG. 1, inserted between the adjacent portions of adipose tissue at the cell injection site, with the tissue separating members of the device deployed in the expanded configuration and separating the adjacent portions of adipose tissue from each other.
Figure 18:
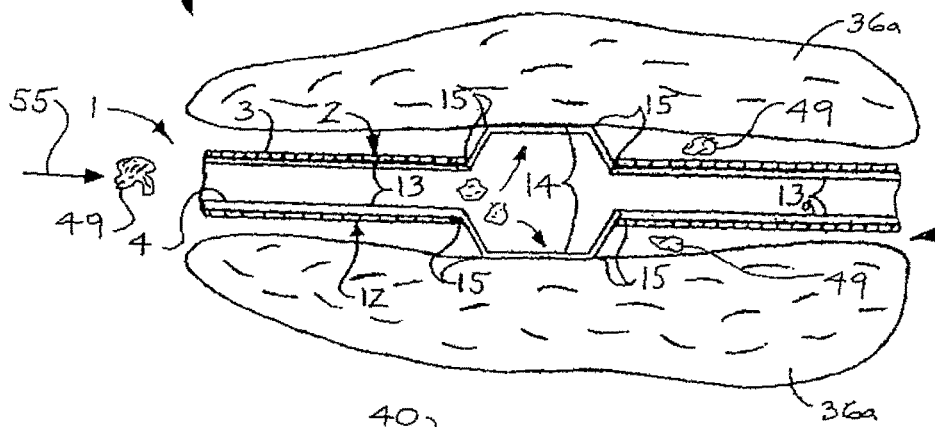
FIG. 18 is a longitudinal sectional view of the sectioned portion of the illustrative tissue transfer device illustrated in FIG. 1, with the tissue separating members of the device deployed in the expanded configuration and more particularly illustrating injection of the harvested tissue regenerative cells into the cell injection site with mechanical agitation of the cells.

A small incision (not illustrated) is next made in the skin of the patient 32 at the cell injection site 36, and the cannula 2 is inserted through the incision. The driving mechanism 18 (FIG. 1) of the device 1 is operated to buckle or expand the expansion segments 14 of the tissue separating members 12 through the respective expansion segment openings 8 in the cannula 2 to engage and separate the portions of injection site adipose tissue 36a from each other, as illustrated in FIGS. 17 and 18. The pump 28 of the device 1 is then operated to generate positive pressure 55 which injects the tissue regenerative cells 49 from the tissue reservoir 24 through the tissue reservoir conduit 26, the cannula interior 4 of the cannula 2 and the expansion segment openings 8, respectively, into the tissue space 58 formed by the expansion segments 14. As illustrated in FIG. 18, in some embodiments, as the tissue regenerative cells 49 are injected into the tissue space 58, the tissue regenerative cells 49 may be subjected to mechanical agitation by manual bidirectional movement 60 of the device 1. This action may increase the quantity or proportion of the tissue regenerative cells 49 which are subject to injury before they enter the tissue space 58.

After the tissue regenerative cells 49 are injected into the cell injection site 36, the expansion segments 14 are retracted into the respective expansion segment openings 8 and the cannula 2 is removed from the patient 32. At the cell injection site 36, the injured tissue regenerative cells 49 release soluble factors which recruit and activate other tissue regenerative cells and bone-marrow derived stem cells in the cell injection site 36. The released factors promote angiogenesis and adipogenesis, filling and restoring the original appearance of the cell injection site 36.

The required quantity of tissue regenerative cells 49 which is to be injected at the cell injection site 36 may depend on such factors as the severity, size and number of the affected area or areas at the cell injection site or sites 36 in need of rejuvenation. In cases of mild or moderate damage, injury, wear or aging of the affected area at the cell injection site 36, treatment may require harvest and injection of the tissue regenerative cells 49 in a single harvesting and injecting transfer. In more severe cases, it may be deemed necessary to obtain tissue regenerative cells 49 from one or more cell harvest sites for injection at one or more cell injection sites 36 in successive harvesting and injecting transfers to ensure injection of a sufficient quantity of tissue regenerative cells 49 at the cell injection site or sites 36 for full rejuvenation.

Referring next to FIGS. 6-9 of the drawings, another illustrative embodiment of the tissue transfer device is generally indicated by reference numeral 1a. The expansion segment openings 8 of the device 1a may be disposed generally adjacent to a distal cannula end 2a of the cannula 2. The tissue separating members 12 may terminate on a stationary connecting portion 20 which may be provided in the cannula interior 4 between the expansion segment openings 8 and the distal cannula end 2a. Accordingly, upon operation of the device 1a, longitudinal movement of the tissue separating members 12 toward the connecting portion 20 causes the expansion segments 14 to expand or buckle outwardly through the respective expansion segment openings 8 in the cannula 2. Operation of the device 1a may be as was heretofore described with respect to the device 1 in FIGS. 10-18.

Figure 19:
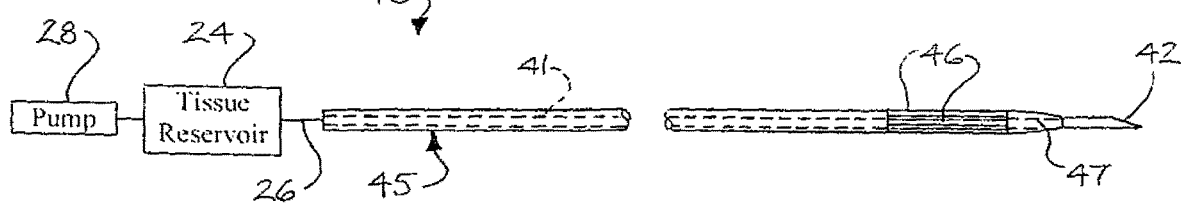
FIG. 19 is a partially schematic and sectioned side view of an alternative illustrative embodiment of the tissue transfer devices.
Figure 20:
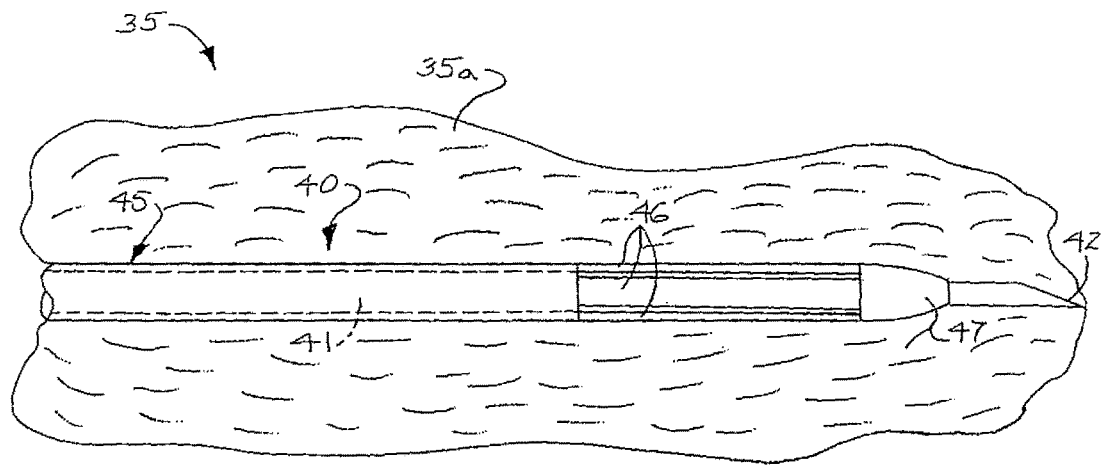
FIG. 20 is a side view, partially in section, of a sectioned portion of the illustrative tissue transfer device illustrated in FIG. 19, inserted between adjacent portions of adipose tissue at the cell harvest site of a patient with the tissue separating members of the device initially deployed in the retracted configuration preparatory to separation of the adipose tissue portions.
Figure 21:
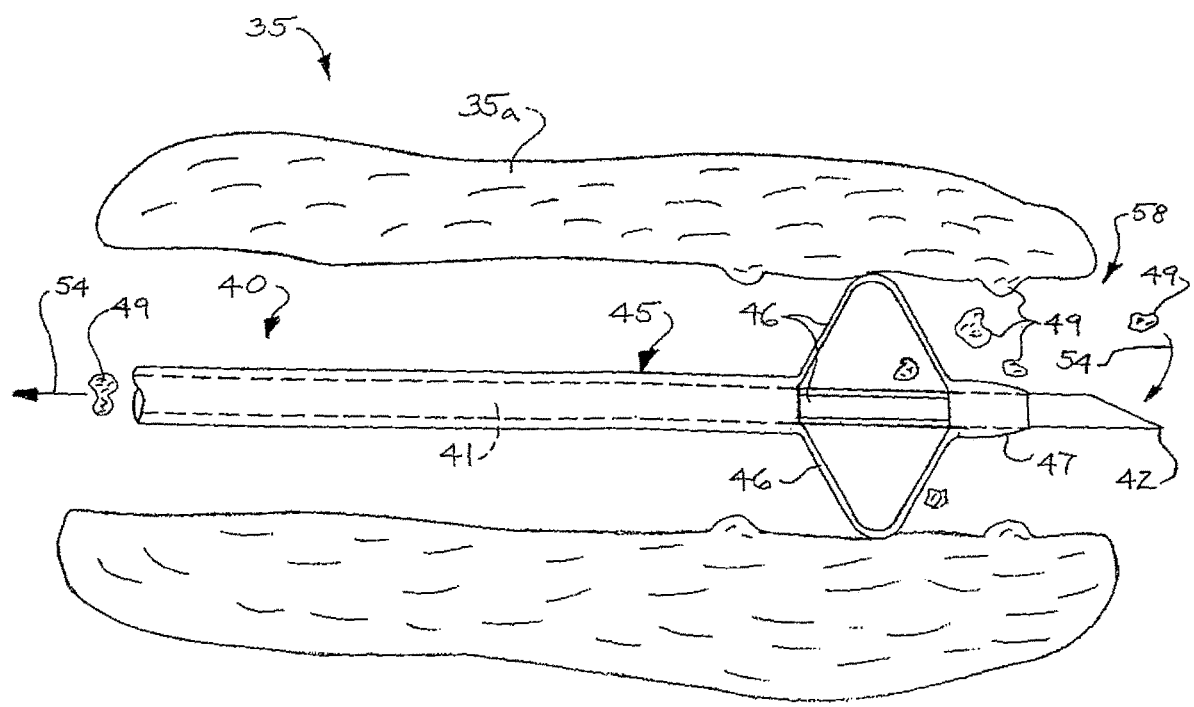
FIG. 21 is a longitudinal sectional view of the sectioned portion of the illustrative tissue transfer device illustrated in FIG. 19, with the tissue separating members of the device deployed in the expanded configuration and more particularly illustrating aspiration of tissue regenerative cells from the cell harvest site after separation of the tissue.

Referring next to FIGS. 19-22 of the drawings, an alternative illustrative embodiment of the tissue regeneration devices, hereinafter device, is generally indicated by reference numeral 40. The device 40 may include a generally elongated cannula 41 having a sharpened and open cannula tip 42. A cannula sheath 45 may be slidably disposed over the cannula 41. The cannula sheath 45 may have a sheath tip 47 which is stationary on the cannula 41 at the cannula tip 42. Multiple elongated, flexible tissue separating members 46 may extend between the sliding cannula sheath 45 and the stationary sheath tip 47. Accordingly, sliding of the cannula sheath 45 on the cannula 41 toward the stationary sheath tip 47 causes the tissue separating members 46 to expand or buckle outwardly from the cannula 41 in a curved or bowed configuration, as illustrated in FIGS. 20 and 21. Conversely, sliding of the cannula sheath 45 on the cannula 41 away from the sheath tip 47 causes the tissue separating members 46 to retract and straighten between the cannula 41 and the sheath tip 47, as illustrated in FIGS. 19 and 20.

As illustrated in FIG. 19, a tissue reservoir 24 may be disposed in fluid communication with the cannula 41 such as through a tissue reservoir conduit 26. A pump 28 may be disposed in fluid communication with the tissue reservoir 24. The pump 28 is operable to selectively apply a partial vacuum or negative pressure 54 (FIG. 21) or positive pressure 55 (FIG. 22) to the cannula 41 and the cannula tip 42 for purposes which will be hereinafter described.

Exemplary application of the device 40 may be as was heretofore described with respect to the device 1 in FIGS. 10-18. As illustrated in FIG. 20, the cannula 41 and the cannula sheath 45 of the device 1 are inserted through an incision (not illustrated) at the cell harvest site 35 (FIG. 10) of a patient. As illustrated in FIG. 21, inside the cell harvest site 35, the tissue separating members 46 are deployed outwardly to separate the adjacent portions of harvest site adipose tissue 35a. This may be accomplished by manually sliding the cannula sheath 45 forwardly on the cannula 41 such that the tissue separating members 46 buckle or expand outwardly and engage and separate the portions of harvest site adipose tissue 35a from each other.

As illustrated in FIG. 21, the pump 28 (FIG. 19) may be operated to draw negative pressure 54 on the cannula 41 and aspirate the tissue regenerative cells 49 through the cannula tip 42, the cannula 41 and the tissue reservoir conduit 26 (FIG. 19) and discharge the tissue regenerative cells 49 into the tissue reservoir 24, respectively. The negative pressure 54 which is applied by the pump 28 (FIG. 1) of the device 1 pulls or aspirates the pericytes 52 from the capillaries 50 (FIG. 15A) harvest site adipose tissue 35a through the cannula 41 and tissue reservoir conduit 26 and into the tissue reservoir 24, respectively, slightly injuring without inducing apoptosis in the pericytes 52. After the desired quantity of tissue regenerative cells 49 has been harvested from the cell harvest site 35 and collected in the tissue reservoir 24, the cannula sheath 35 may be slid on the cannula 41 toward the sheath tip 47 to straighten and collapse or return the tissue separating members 46 to the retracted position, as illustrated in FIG. 20, and the cannula 41 withdrawn from the cell harvest site 35.

Figure 22:
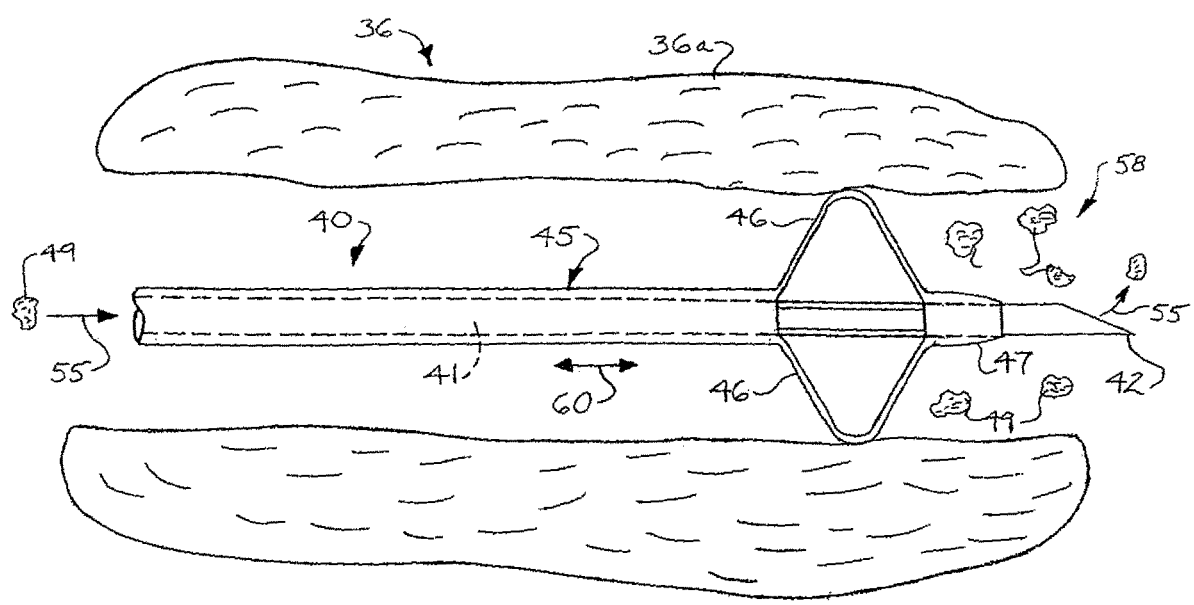
FIG. 22 is a longitudinal sectional view of the sectioned portion of the illustrative tissue transfer device illustrated in FIG. 19, with the tissue separating members of the device deployed in the expanded configuration and more particularly illustrating injection of the harvested tissue regenerative cells into the cell injection site after separation of the tissue.

The cannula 41 and cannula sheath 45 are inserted through an incision (not illustrated) at the cell injection site 36 of the patient. The cannula sheath 45 is slid forwardly on the cannula 41 toward the sheath tip 47 to buckle or expand the tissue separating members 46 of the cannula sheath 45 outwardly to engage and separate the portions of injection site adipose tissue 36a from each other, as illustrated in FIG. 22. The pump 28 of the device 40 is then operated to generate positive pressure 55 which injects the tissue regenerative cells 49 from the tissue reservoir 24 through the tissue reservoir conduit 26, cannula 41 and cannula tip 42, respectively, into the tissue space 58 formed by the tissue separating members 46. As further illustrated in FIG. 18, in some embodiments, as they are injected into the tissue space 58, the tissue regenerative cells 49 may be subjected to mechanical agitation such as by manual bidirectional movement 60 of the device 1. This agitation action may increase the quantity or proportion of the tissue regenerative cells 49 which are subject to injury before they enter the tissue space 58.

After the tissue regenerative cells 49 have been injected into the cell injection site 36, the tissue separating members 46 are retracted against the cannula 41 and the device 1 is removed from the cell injection site 36. Inside the cell injection site 36, the injured tissue regenerative cells 49 release soluble factors which recruit and activate other tissue regenerative cells and bone-marrow derived stem cells in the cell injection site 36. The released factors stimulate angiogenesis and adipogenesis, filling and restoring the original appearance of the cell injection site 36.

Figure 23:
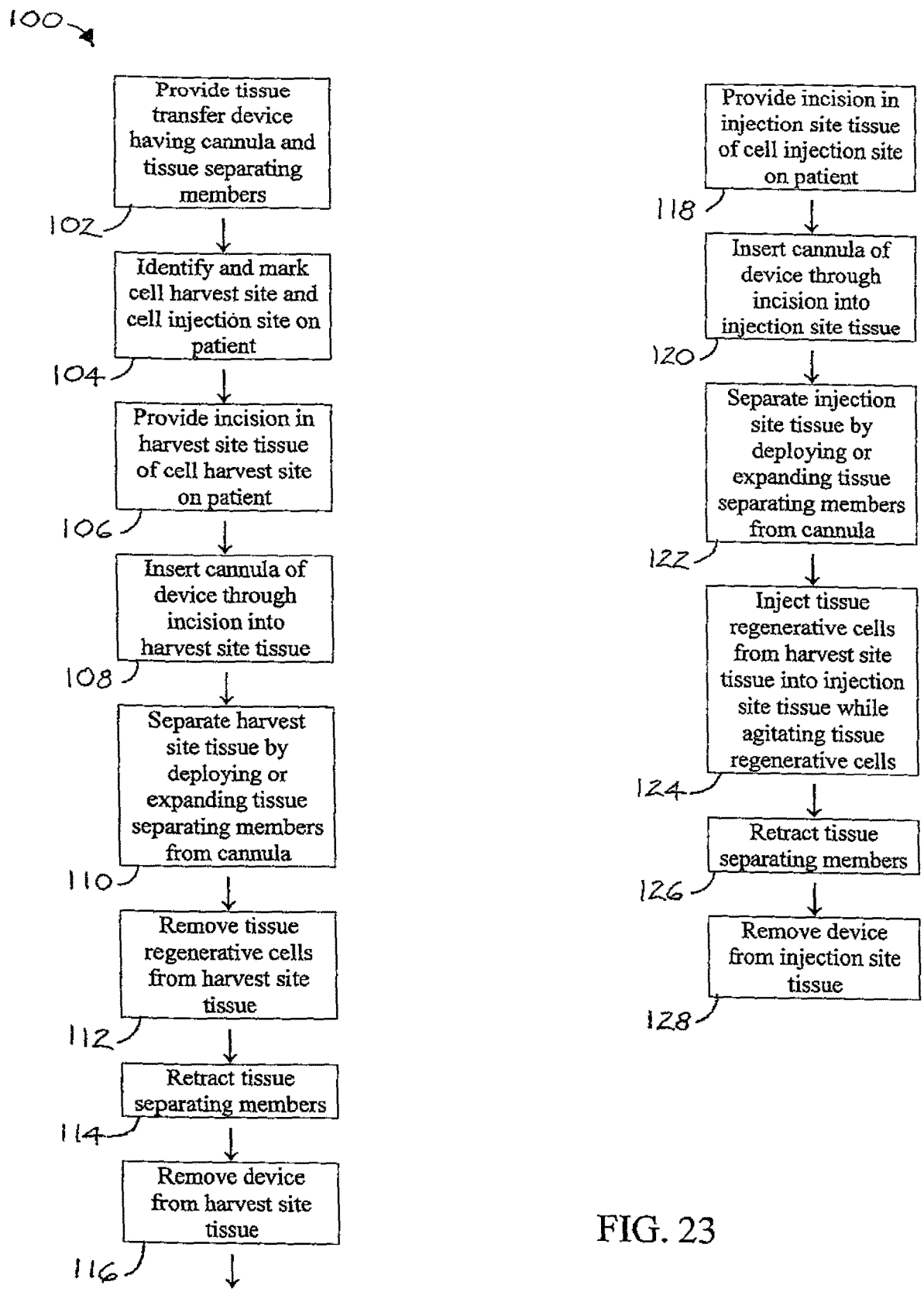
FIG. 23 is a flow diagram of an illustrative embodiment of the tissue rejuvenation methods.

Referring next to FIG. 23, a flow diagram 100 of an illustrative embodiment of the tissue rejuvenation methods illustrated. In block 102, a tissue transfer device is provided. The tissue transfer device may include a cannula and selectively expandable and retractable tissue separating members on the cannula. In block 104, a cell harvest site and a cell injection site are identified and marked on a patient. In block 106, an incision is made in the harvest site tissue at the cell harvest site on the patient. In block 108, the cannula of the tissue transfer device is inserted through the incision into the harvest site tissue. In block 110, the harvest site tissue is separated by deploying or expanding the tissue separating members from the cannula. In block 112, tissue regenerative cells are removed from the harvest site tissue. In block 114, the tissue separating members of the tissue transfer device are retracted. In block 116, the device is removed from the harvest site tissue.

In block 18, an incision is made in the injection site tissue at a cell injection site on the patient. In block 120, the cannula of the device is inserted through the incision into the injection site tissue. In block 122, the injection site tissue is separated by deploying or expanding the tissue separating members from the cannula. In block 124, the tissue regenerative cells from the harvest site tissue are injected into the injection site tissue. In some embodiments, the tissue regenerative cells may be injected into the injection site tissue while subjecting the tissue regenerative cells to mechanical agitation. Mechanical agitation of the cells may be accomplished by repeatedly manually moving the device in a bidirectional motion as the tissue regenerative cells are injected into the injection site tissue. In block 126, the tissue separating members are retracted. In block 128, the device is removed from the injection site tissue.

While illustrative embodiments of the disclosure have been described above, it will be recognized and understood that various modifications can be made in the disclosure and the appended claims are intended to cover all such modifications which may fall within the spirit and scope of the disclosure.

What is claimed is:

1. A tissue transfer device, comprising:
   a cannula having a cannula wall, a cannula interior enclosed by the cannula wall and a distal cannula end closing the cannula interior, the distal cannula end disposed in fixed relation to the cannula wall;
   a plurality of tissue separating members extending longitudinally through the cannula interior and outwardly extendable from the cannula interior through the cannula wall, each of the plurality of tissue separating members comprises an elongated rod or strip of flexible material and a proximal shaft segment disposed in slidable axial relation to the cannula, a distal shaft segment disposed in fixed relation to the cannula and an expansion shaft segment extending between the proximal shaft segment and the distal shaft segment, the expansion shaft segment of each corresponding one of the plurality of tissue separating members extendable and capable of expanding or buckling outwardly from the cannula upon movement of the proximal shaft segment relative to the cannula as the distal shaft segment remains stationary relative to the cannula;
   a tissue reservoir disposed in fluid communication with the cannula interior of the cannula; and
   a pump disposed in fluid communication with the tissue reservoir.

2. The tissue transfer device of claim 1 further comprising a plurality of expansion segment openings in the cannula wall, and wherein the expansion shaft segment of each corresponding one of the plurality of tissue separating members is extendable through a corresponding one of the plurality of expansion segment openings upon movement of the proximal shaft segment relative to the cannula toward the expansion shaft segment.

3. The tissue transfer device of claim 2 wherein each of the plurality of expansion segment openings has a generally elongated, slotted shape.

4. The tissue transfer device of claim 2 wherein the plurality of expansion segment openings comprises four expansion segment openings extending through the cannula wall generally at 90 degrees with respect to each other around a cross-sectional circumference of the cannula wall.

5. The tissue transfer device of claim 1 further comprising a pair of bend lines in each of the plurality of tissue separating members between the expansion shaft segment and the proximal shaft segment and between the distal shaft segment and the expansion shaft segment, respectively.

6. The tissue transfer device of claim 1 further comprising a driving mechanism engaging the proximal shaft segment, the driving mechanism adapted to slide the proximal shaft segment relative to the cannula.

7. The tissue transfer device of claim 1 wherein each of the plurality of a tissue separating members includes an elongated rod or strip of flexible metal or other material.

8. A tissue transfer device, comprising:
a cannula having an open distal cannula end;
a tissue reservoir disposed in fluid communication with the cannula;
a pump disposed in fluid communication with the tissue reservoir; and
a cannula sheath extending over and slidable with respect to the cannula, a sheath tip extending over the cannula, the sheath tip stationary on and with respect to the cannula and a plurality of elongated, flexible, discrete tissue separating members extending over the cannula and spanning between the cannula sheath and the sheath tip, the plurality of tissue separating members extendable and capable of expanding or buckling outwardly from the cannula by sliding the cannula sheath on the cannula toward the sheath tip and the plurality of tissue separating members retractable and capable of straightening between the cannula sheath and the sheath tip by sliding the cannula sheath on the cannula away from the sheath ti as the sheath tip remains stationary relative to the cannula.

9. The tissue transfer device of claim 8 wherein each of the plurality of tissue separating members includes an elongated rod or strip of flexible metal or other material.

\* \* \* \* \*